United States Patent [19]

Carlson

[11] 4,209,299
[45] Jun. 24, 1980

[54] METHOD AND APPARATUS FOR DETERMINATION OF VOLATILE ELECTROLYTES

[75] Inventor: Robert M. Carlson, Davis, Calif.

[73] Assignee: The Regents of The University of California, Berkeley, Calif.

[21] Appl. No.: 879,156

[22] Filed: Feb. 21, 1978

[51] Int. Cl.[2] ..................... G01N 27/40; G01N 27/56; G01N 33/00
[52] U.S. Cl. .................. 23/230 R; 204/1 T; 422/68; 422/76; 422/98; 422/81
[58] Field of Search ............. 23/230 R, 253 R, 232 E, 23/254 E, 253 R; 204/1 T; 195 P; 210/22, 321 A, 96 R, 96 M; 324/30 R, 30 A, 30 B; 422/98, 68, 76, 81

[56] References Cited

U.S. PATENT DOCUMENTS

| | | | |
|---|---|---|---|
| 2,999,673 | 9/1961 | Kessler | 23/253 R X |
| 3,495,943 | 2/1970 | Kapff | 23/253 R X |
| 3,572,994 | 3/1971 | Hochstrasser | 23/253 R X |
| 4,003,705 | 1/1977 | Buzza et al. | 23/253 R X |
| 4,025,308 | 5/1977 | Holman et al. | 23/253 R X |
| 4,131,428 | 12/1978 | Diggens | 23/230 R |

OTHER PUBLICATIONS

Technicon Auto Analyzer II–Continuous-Flow Analytical System, 1976.

*Primary Examiner*—Michael S. Marcus
*Attorney, Agent, or Firm*—Owen, Wickersham & Erickson

[57] ABSTRACT

Quantitative determination of a particular type of volatile material in a liquid is determined by first transferring the desired volatile, suppressing other volatiles if necessary, to a liquid of known conductivity, such as deionized, degassed water. Transfer is through a gas-permeable, liquid-impermeable membrane. Then the electrical conductivity of the water to which the volatile material has been transferred is determined. Continuous stream processing is feasible. An instrumental assembly suitable for this determination is provided.

15 Claims, 14 Drawing Figures

METHOD AND APPARATUS FOR DETERMINATION OF VOLATILE ELECTROLYTES

BACKGROUND OF THE INVENTION

This invention relates to method and apparatus for the determination of the amount of a particular type of volatile electrolyte present in a stream. It includes a continuous flow system in which a volatile component that will dissolve in water or other solvent to form an electrically conducting solution is transferred from a sample stream to a deionized water (or other) stream by diffusion through a gas permeable membrane or air gap. The water stream with the dissolved component passes through an electrical conductivity cell for quantification of the concentration of the volatile component in the original sample.

The invention may, for example, be used for Kjeldahl nitrogen, i.e., ammonium nitrogen, determination. It may also be used for determination of dissolved carbon dioxide. It can be used to determine any constituent that will diffuse through a membrane (or air gap) as a gas and that will dissolve in a sample receiving stream to produce a solution that will conduct electricity. Tests have shown its usefulness in detecting methylamine and dimethylamine when the sample stream is mixed with alkali, and acetate when the sample stream is mixed with acid. The invention can be used to determine nitrate nitrogen and ammonium by inserting a small column of Devarda alloy in the sample stream to reduce the nitrate to ammonium.

The invention also responds to atmospheric carbon dioxide levels when air is pumped through the sample and reagent channels, in place of solutions. Thus, the invention can be used as a gas analyzer. It can be made selective as a gas analyzer, at least for some constituents, by selectively absorbing unwanted constituents that produce a response from the gas sample stream.

Heretofore, the leading systems for detection of volatile components in liquids have involved either colorimetry or gas-sensing electrodes. For example, one available instrument can be set up with either one of these two detection systems. In testing for the ammonium ion by the colorimetry system, the sample stream is mixed with reagents that react with ammonium to produce a new, colored, compound that absorbs light. This combined stream then passes through a cell where the amount of light that is absorbed by the stream is measured. The light absorbed is then related to the concentration of ammonium in the original sample stream. In such a system, the original sample must be free of suspended material (turbidity) or colored substances, as they would also absorb light and lead to error. If the sample is not free of turbidity and color, it must be pretreated to remove these before processing on the instrument.

In its other mode, this prior-art instrument uses a gas-sensing ammonia electrode. Here the sample stream is mixed with a reagent and passed through a flow-through fitting attached to the electrode. The electrode consists of a pH-sensitive surface coated with a thin film of solution and separated from the sample by a gas permeable membrane. Ammonia from the sample diffuses through the membrane and dissolves in the thin film of solution causing a change of pH. This pH change is related to the ammonium concentration in the original sample. While this system will tolerate color and turbidity, it has the disadvantage of not being very stable; that is, the detection system tends to drift and so it must be recalibrated frequently. These gas-sensing ammonia electrodes also require frequent servicing; they must be disassembled, cleaned, the membrane replaced, and then the electrode reassembled.

Another major disadvantage is that this prior-art system cannot tolerate samples with even moderate concentrations of dissolved substances (salts, acids, sugars, etc.). Samples with high concentration of dissolved substances must be diluted before processing. If a sample with considerable dissolved substances is run, the results are in error, and the ammonia electrode exhibits a memory effect; several samples following the one with considerable dissolved substances are also in error.

Various procedures for the determination of ammonia by electrical conductivity measurements have been reported. In 1942 Hendricks et al in 5 *Ind. Eng. Chem. Anal. Ed.* 23-26 described a vacuum distillation procedure in which the ammonia was collected in boric or sulfuric acid and determined by the change in conductivity of the acid. In a similar procedure, Appleton 42 *Chemist-Analyst* 4-7 (1953), distilled ammonia into boric acid, diluted the solution to known volume, and determined ammonia from conductivity changes. Shaw and Staddon in 35 *Jour. Exper. Biol.* 85-95 (1958) used a diffusion cell to transfer ammonia from the sample to sulfuric acid for its subsequent determination by conductivity. Friedl in 48 *Anal. Biochem.* 300-306 (1972) determined ammonia from the rate of change of conductivity of a small volume of sulfuric acid as it absorbed ammonia from a sample in a diffusion cell. Separation of ammonia by distillation (See Keay et al 94 *Analyst* 895-899 (London, 1969) and dialysis (Technicon Corporation, Tarrytown, N.Y., *Industrial Method* No. 330-74A/A) have been employed in automated colorimetric methods.

Diffusion through plastic tubing has been reported as a technique for separating gaseous components of samples. Kollig et al, 9 *Environ. Sci. Technol.* 957-960 (1975) used silicone rubber tubing in a device for sampling waters for dissolved oxygen, nitrogen and carbon dioxide determinations. Scarano and Calcagno, 47 *Anal. Chem.* 1055-1065 (1975) determined dissolved carbon dioxide from pH changes in a bicarbonate solution flowing through a Teflon tube immersed in the sample. Westover et al, 46 *Anal. Chem.* 568-571 (1974) described a sampling device for mass spectrometry that was based on gas permeation through silicone rubber hollow fibers.

SUMMARY OF THE INVENTION

In this invention, a method is provided for determining the amount of a particular type of volatile electrolyte present in a sample by:

(1) transferring to a second liquid of known electrical conductivity a volatile electrolyte in the sample, by means of a gas-permeable membrane that does not pass liquid, the transfer being made over a predetermined time interval, and (2) determining the change in electrical conductivity of the second liquid.

In case other volatile material is present, step (1) above is preceded by adding to the sample a material that suppresses these other volatiles.

The method can be practiced on a stream basis by:

(1) mixing a sample stream at constant flow with a reagent at constant flow, the reagent being one that converts unwanted volatile electrolytes which may be present in the sample stream, that is, volatile electrolytes different from the particular type to be determined, into non-volatile substances (in addition to suppressing these unwanted volatile electrolytes, the reagent may and preferably does enhance the volatility of the particular type to be determined), (2) adjusting the resultant sample stream to a predetermined temperature at which the particular electrolyte to be determined is suitably volatile, (3) purifying a stream of deionized water to remove foreign substances and particulate matter therefrom, (4) adjusting the purified stream of water to the predetermined temperature of (2), (5) degasifying the purified stream of water, (6) passing the sample stream and the purified degasified water at the predetermined temperature along a path while separating them from each other by a liquid-impermeable, gas-impermeable membrane, so as to transfer the desired volatile material from the sample stream to the water and preferably until a steady state is reached, and (7) then afterwards determining the conductivity of the water stream.

Apparatus for practicing the method may include:

(a) permeation means defining an isolated path of substantial length and including membrane means along the full length of the path for preventing passage of a liquid therethrough, while passing a gas therethrough, (b) means for pumping at a constant rate at least three liquids, namely water, the sample stream, and the reagent for changing the other types of volatile electrolytes into non-volatile substances, (c) mixing means for mixing the reagent with the sample stream in a constant proportion, (d) purifying means for deionizing the water and removing particulate matter therefrom, (e) heat-exchange means for simultaneously bringing to the same predetermined temperature the purified water and the reagent-reacted water stream, (f) degassing means for removing substantially all gas from the water stream, (g) means for applying the water stream to one end of the path and the sample stream to one end of the path and on opposite sides of the membrane means from each other, for flow of both (co-currently or counter-currently) along the path, and (h) means for determining the electrical conductivity of the water stream leaving the path.

If the method is to be practiced on a batch basis, then the apparatus can, of course, be simplified and adapted to that basis.

Like the instrument using colorimetry or gas-sensitive electrodes, my invention uses, or can use, continuous flow analysis, automatic samplers, peristaltic pumps, some form of temperature control, and strip chart recorders to log the instrument response. Also like that prior-art instrument, my invention involves mixing the sample stream with a reagent stream or streams. Further, my invention can also run unattended except for start-up, changing trays of samples, and shut down.

However, the present invention has the following advantages over such prior-art systems:

1. There is no interference from turbid or colored samples. Instruments based on colorimetric detectors require the sample generally to be color-free and non-turbid. Sample color and turbidity have no effect on an instrument of the present invention; so preliminary sample preparation is minimized.

2. High concentrations of total dissolved substances cause no problems.

3. Memory effects (errors caused by carry over from previous sample) are no problem.

4. There is very high stability, practically no drift, and a highly stable base line. Instruments based on potentiometric detectors require frequent standardization and are subject to drift in the response. Instruments of the present invention are much more stable than potentiometric instruments and are much less troubled with electrical interference.

5. Much less maintenance is required.

6. The instrument is very rugged and durable, and it is easy to use by unskilled workers. Compared with either the colorimetric systems or the potentiometric systems, an instrument of the invention is more rugged and requires less maintenance.

7. Simpler and faster start-up and shut-down procedures are established.

8. Accuracy and precision is equal to or better than the prior-art instruments, even under what to them are favorable conditions.

9. The present invention can be practiced by much less expensive apparatus.

The detection system is a very important feature of the invention: a combination for transferring the ammonia (or other constituent, such as carbon dioxide) to a solvent and measuring the change in the electrolytic conductivity of the solvent caused by such transfer.

DESCRIPTION OF PREFERRED EMBODIMENTS

A suitable apparatus

Figure 1:
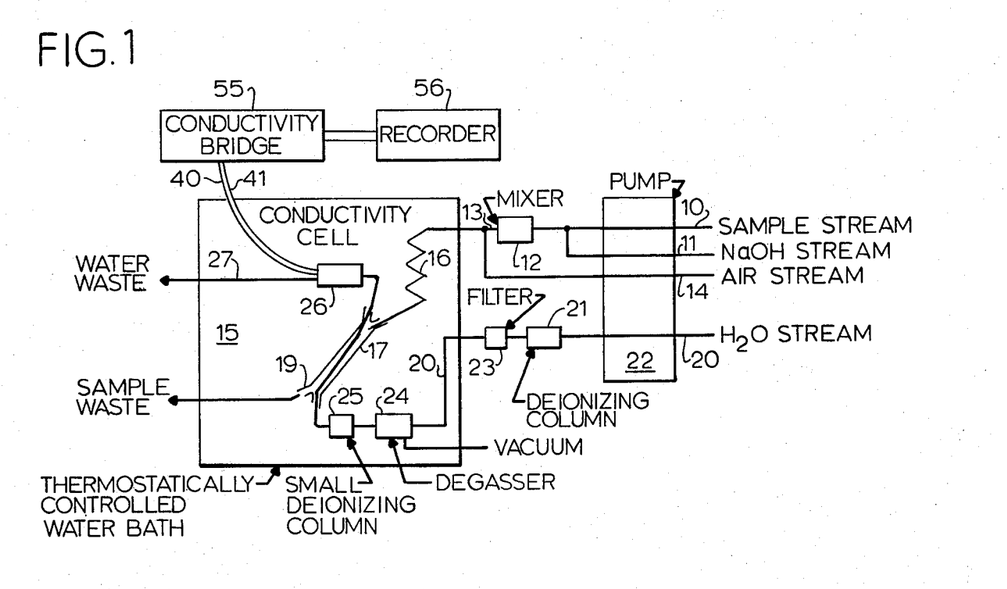
FIG. 1 is a block diagram of an apparatus embodying the principles of the invention.
Figure 2:
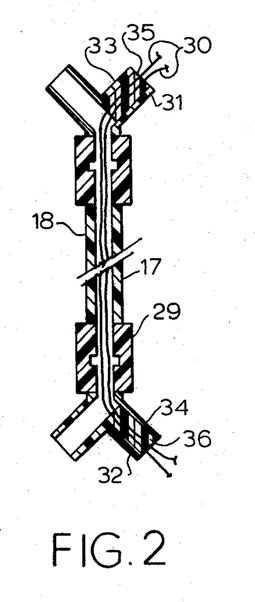
FIG. 2 is an enlarged view in section of a silicone fiber permeation unit for use in the invention.
Figure 3:
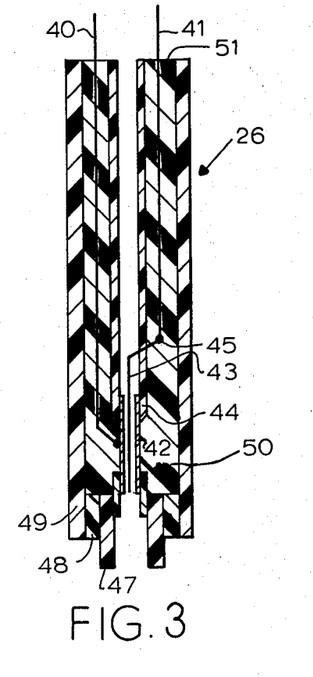
FIG. 3 is a view in section of an electric conductivity cell embodying the principles of the invention.

FIGS. 1–3 show an instrument for measuring Kjeldahl nitrogen. A sample stream 10 in this instance is a sample resulting from Kjeldahl digestion of biological material or soil or other suitable materials.

The sample stream 10 and a stream 11 containing a reagent such as NaOH for suppressing other volatiles and enhancing ammonia volatility are mixed in a mixer 12. The mixer 12 may be a micro, magnetic stir-bar mixing device constructed as described by Gugger and Mozersky in 45 *Anal. Chem.* 1575–1576 (1973). A stream 14 of air is injected into the mixed sample stream 13 just as it exits from the mixer 12. The stream 13 then enters a thermostated water bath 15 (e.g., a Themonix Model 1480 Constant Temperature Circulator) and passes through a coil 16 of tubing to bring the sample to the bath temperature. The coil 16 may be made from glass or stainless steel tubing 50 cm long, and having an inside diameter of 1 or 2 mm, and a wall about 1 mm thick. The stream 13 then passes into a tube 17 containing a membrane transfer assembly 18. When the sample leaves the tube 17, it is discharged to waste at 19.

The size of the tubing 16 is preferably selected so that the solution flow is turbulent rather than laminar. This provides a sharper transition between samples, because there is less intermixing between samples, yet the tubing bore (0.042 inches or 1 mm, inside diameter) is not so small that high pressure is required to maintain the solution flow. With turbulent flow, there is no need to segment the sample stream with air bubbles to minimize intermixing of samples. Laminar flow systems (which are used by others) require segmenting to minimize intermixing of samples. Use of air injection does slightly shorten the time to obtain the response after the sample is introduced. This is due to the increase in the speed at which the sample passes through the instrument. Injection of air has no effect on the magnitude of the response and debubbling or removal of the air before the sample reaches the detector system is not required.

A stream 20 of deionized distilled water is pumped through a small column 21 of mixed-bed resin for further polishing. A single four-channel pump 22 may be used for all the streams 10, 11, 14, and 20, for example, the pump may be a Gilson Model HP-4, four-channel peristaltic pump. The small column 21 may be constructed from a polypropylene barrel of a 6 ml disposable syringe and may contain resin supported in the column by disks of porous polyethylene. As the water stream 20 leaves this column, it passes through a filter 23, which may be a 25 mm Swinnex filter holder with a Millipore type AA membrane, to remove any particulate matter that might clog the hollow fibers of the assembly 18.

The water stream then enters the thermostated bath 15, and passes through a degassing unit 24 and another small, mixed-bed deionizing column 25, which may be constructed like the column 21, but preferably with a 1 ml syringe barrel. Then it enters the tube 17 through the membrane assembly 18 and flows to a conductivity cell 26, whence it is discharged to waste at 27. The degassing unit 24 may comprise a silicone rubber hollow fiber minitube, e.g., a bundle of semipermeable, hollow-bore, silicone rubber fibers (Cf. U.S. Pat. Nos. 2,972,349 and 3,228,876) with the outer chamber connected to a house vacuum system through a 1 liter vacuum flask ballast and a check valve. Inclusion of the degasser prevents air bubble formation in the assembly 18 and later in the conductivity cell 26 when the bath 15 is operated at elevated temperature. The sample, reagent and water transmission lines were cut from 0.042 in. ID polyethylene tubing, to provide the desired turbulent flow. Connections were made with silicone rubber or vinyl tubing.

The degassing component is helpful when the temperature bath is operated at temperatures considerably above ambient. As water temperature is raised, the solubility of gases, such as, oxygen and nitrogen decreases. Without the degasser, bubbles could form in the fibers and in the electrical conductivity cell. This would lead to a noisier response. When operated near (e.g., within 5° C. of) ambient temperatures, the degasser may be omitted; however, general use of the degasser does insure sufficient removal of dissolved gases to avoid problems, and so, use of the degasser is desirable.

The deionizing units and membrane filter in the water line are not needed if very clean water which is free of electrolytes (including dissolved carbon dioxide) is always used. The inclusion of these components in the water stream provides insurance that particle-free water which approaches conductivity water passes through the fibers to collect the volatile electrolyte being determined. This is especially helpful when the instrument is used to determine very low concentration samples (e.g., solutions in which ammonium approaches 0.1 ppm).

The method is based on the transfer of ammonia by diffusion from the sample stream 13 in the assembly 18 through silicone rubber hollow fibers 30 into the flowing stream 20 of water, followed by detection by electrical conductivity in the cell 26. The apparatus is useful for ammonia determination in water samples, for dissolved carbon dioxide determination, and for other determinations, too.

The gas permeation assembly 18 (See FIG. 2) may be prepared by attaching an ⅛ inch inside diameter polypropylene Y-connector 31,32 to each end of a 50 cm length of 0.062 inch ID small bore polyethylene tubing 17 with short sections of silicone rubber tubing 29 (1/16 inch ID, 3/16 inch OD). Six strands of Dow Corning silicone rubber hollow fibers 30 were cut to a length 10 cm greater than twice the length of the polyethylene tube 17 with its attached Y connectors 31 and 32. The fibers 30 were passed through a loop of thread, doubled over and then carefully drawn through one branch 33 of a Y connector 31, the polyethylene tube 17 and out one branch 34 of the Y connector 32 at the other end. The fibers 30 were potted into the branches 33 and 34 of the Y connectors 31 and 32 with clear Dow Corning silicone rubber sealer 35 and 36. After allowing the sealers 35 and 36 to cure for four days, the excess sealer and silicone fibers were cut off flush with the ends of the branches 33 and 34 of the Y connectors 31 and 32. The sample flows around the fibers 30 and the water through them and on to a suitable electrical conductivity cell 26 shown in FIG. 3.

This conductivity cell 26 was designed for a very small volume, of about 10 microliters. Thus, the water stream passing through it very rapidly changes in the cell 26 (100 changes per minute when the water flow rate is 1 ml per minute). This cell structure enhances the time response of the instrument and thus, permits the high rate of sample processing.

To construct the cell 26, leads 40 and 41 were soldered to a 6 mm section of 14 gauge-type 304 stainless steel tubing 42 and a piece of 0.8 mm diameter stainless steel wire 43. Stainless steel has been adequate for everything so far tested. However, there may be situations where a noble metal (gold or platinum) might offer advantages over stainless steel. A length of tygon tubing 44 (1/16 inch ID, 1/32 inch wall) was attached to one end of the steel tubing. The steel wire 41 was bent at 45, poked through the vinyl tubing 44 and centered in the steel tubing 42 by slipping a piece of polytetrafluoroethylene small-diameter (Teflon spaghetti) tubing over it (not shown) to make an assembly. Vinyl tubing 47, 48, and 49 of various sizes were assembled, as shown in FIG. 3, to make a well 50 in which the assembly was mounted. The well 50 was then filled with styrene casting resin 51 to hold the electrodes 42 and 43 of the cell 26 rigidly in place. After the casting resin 51 had hardened, the spaghetti tubing 46 used to center the wire electrode was removed. This structure and procedure enables placement of the conductivity cell 26 very close to the outlet of the hollow fiber bundle. The leads 40 and 41 are connected to a suitable conductivity analyzer 55, such as a Markson Science Model 4405 conductivity analyzer, and may be read in various ways, such as a strip chart recorder 56, which may be a Linear Instruments Corp. Model 254 Strip Chart Recorder.

A system of this invention made as described has been found to respond to a sample in less than 90 seconds from the time the sample starts to be pumped. The best prior-art colorimetric system requires from 20 to 30 minutes to respond. The shorter response time enabled by the present invention is much more convenient; there is no waiting to adjust instrument sensitivity for particular samples or to discover problems with the instrument or with the standards or samples.

For Kjeldahl nitrogen, the system just described requires approximately 2 ml of sample. The prior-art colorimetric system requires approximately 4 ml.

If samples of considerably different concentration are run in the same batch, a blank must be run between each sample on the best available prior-art system. This reduces by half the number of samples that can be run in a given time. No blank is required between samples on the system of the present invention.

The system of this invention requires only three or four pumping tubes (depending on whether air injection is used). The prior-art colorimetric system requires at least seven pumping channels, and more if dilutions are required, for the determination of ammonium nitrogen. The prior-art system requires four different reagent solutions for ammonium, the present invention requires only one simple solution. Thus, the pumping arrangement for this invention is much simpler. The simpler system requires less maintenance, and with fewer pumping tubes it is easier to determine which ones need to be replaced, as the occasion arises.

The magnetic stir-bar mixer 12 is much more efficient than the mixing coils used in prior-art devices. The stir-bar mixer 12 almost instantaneously mixes the sample and reagent streams. Mixing coils require a much longer time to thoroughly mix the sample and reagent streams.

The device of the present invention requires much less maintenance than either of the two best prior-art systems (one colorimetric and one with an ion-selective electrode). It is also much more stable than them. They require blanks and standards with each set of samples. The device of this invention can operate for long periods without checking standards because of its inherent stability. Its base line is so stable that blanks only need to be run when setting the instrument up for a particle range of sample composition.

EXAMPLE 1

Example of the way the apparatus of FIGS. 1-3 may be used in a method of the invention for Kjeldehl nitrogen Reagents. All reagents were prepared from analytical reagent grade chemicals. Samples were mixed with 1.5 M NaOH containing 6 g $Na_2EDTA.2H_2O$ per liter. The EDTA (ethylene diamine tetra acetic acid) was added in this particular test to prevent precipitation of polyvalent metal hydroxides and carbonates. It is not always necessary. Carbon dioxide determinations were carried out by mixing the sample with 1 M $HClO_4$.

Operating Procedure. The startup procedure consisted of pumping water through the reagent and sample lines 11 and 10 while the temperature bath 15 stabilized (10 to 15 minutes). These lines 11 and 10 were also later flushed with water for 5 minutes at instrument shutdown. When not in use, the degassing unit 24 was disconnected from the vacuum line to prevent loss of water from the hollow fibers of the assembly 18.

Kjeldahl digestion. 250 mg aliquots (plant tissue samples) were digested in calibrated 75 ml digestion tubes in a block digestor. The digestion mixture was 5 ml $H_2SO_4$, 3.5 g $K_2SO_4$, and 40 mg $CuSO_4$. One selenized boiling chip was added to each tube. The samples were heated to 370° C. and held at this temperature for 2 hours. After cooling, they were diluted to 75 ml and mixed.

Results and decision. Even though the surface area of the fiber bundle is large (estimated to be 47 $cm^2$ for a 50 cm-long unit containing 12 fibers), the pumping rate required to allow the water passing through the fibers to reach equilibrium with the sample is too slow for rapid processing of samples. The system depends on a steady state transfer of gas rather than equilibration of the water stream with the sample stream. The diffusion of gas through the fiber walls is temperature-dependent, as is the electrical conductivity of the resulting ammonium hydroxide or carbonic acid solutions. The overall temperature dependence was determined by noting the response to an ammonium standard at various temperatures between 25° and 50°. The response increased by approximately 4% per degree. Hence, a bath 15 that will maintain temperature constant to $\pm 0.01°$ provides adequate control of this variable.

An estimate of the extent of gas transfer was obtained by collecting the water passing through the fibers 30 while a $10^{-3}$ M $NH_4Cl$ was pumped through the unit at 4.98 ml/min mixed with 1.5 M NaOH at 1.17 ml/min. The flow rate of water through the fibers 30 was 0.98 ml/min and the bath temperature was 35°. The water from the fibers 30 was collected in a small volume of 1 M $HClO_4$ to prevent volatilization losses. This solution was then run through the instrument as a sample with appropriate standards to determine the ammonium concentration, which was found to be 2.6% of the ammonium concentration in the $NH_4Cl$/NaOH stream. For adaptation to samples with very low levels of ammonium, the extent of gas transfer could be increased by employing a unit with more and/or longer fibers 30 and by operating at higher temperatures. Decreasing the pumping rate of water through the fibers 30 will also increase the concentration of ammonia in the solution reaching the conductivity cell 26.

Figure 4:
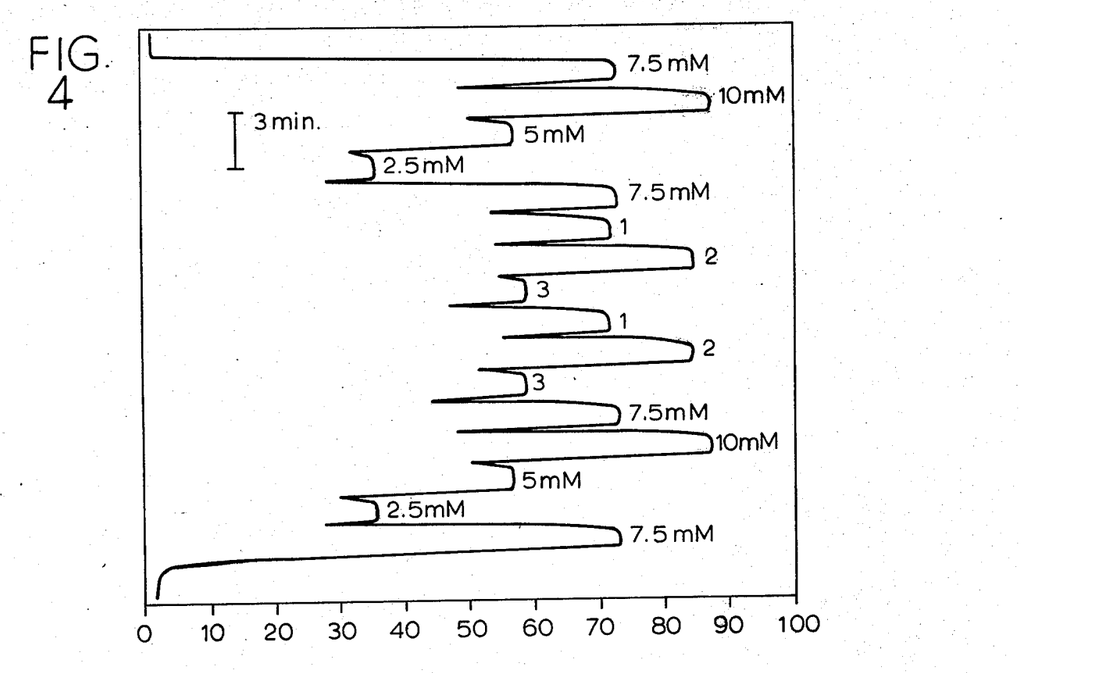
FIG. 4 is a typical strip chart recorder trace for standards and Kjeldahl nitrogen samples, with the standards indicated by millimolar concentration of ammonium, and the samples indicated by number plotting instrument response to ammonium content against time.

In addition to maintaining constant temperature, the pumping rates must be constant (especially that of the water passing through the fibers 30) to obtain stable response. The response time depends on the rate at which sample and reagent are pumped over the fibers 30 and on the rate water is pumped through the fibers 30. Typical sampling time used in this work was 90 seconds with an additional 10 seconds required for the sampler to raise the probe and advance to the next sample. Air is aspirated between samples. This provides a convenient spike in the trace for the recorder 56, this trace separates samples of similar composition. FIG. 4 shows a typical recorder trace.

The effect of the total concentration of salts in the sample stream 10 is an additional variable that requires attention. The partial pressure of ammonia or carbon dioxide will depend on the total salt load. For water samples, the total concentration will be dominated by the NaOH or HClO$_4$ mixed with the sample; so sample-to-sample variation will be small. For digested samples, the sodium sulfate formed in the neutralization of sulfuric acid and the potassium sulfate in the digestion mixture will be major components of the salt load. Standards for these determinations should contain sulfuric acid and potassium sulfate at concentrations similar to those of the samples. The amount of potassium sulfate required can be calculated, but some sulfuric acid is consumed in the digestion so the acid concentration in a few samples should be determined to establish the amount of acid to be added to the standards. As the amount of acid consumed in the digestion will vary somewhat, the effect of variable acid concentration was determined. Ammonium chloride standards were prepared with 30, 60, and 90 ml sulfuric acid per liter. Instrument response decreased 2.5% as acid concentration increased from 30 to 90 ml per liter. The acid concentration for digested samples ranged from 50.5 to 55.5 ml per liter. The effect of this variation is insignificant. Standards were prepared to contain the average acid concentration found in the samples to avoid systematic errors.

Most of the precision and accuracy determinations were done with plant tissue samples that had been carried through the Kjeldahl digestion procedures. Precision was determined by running 39 digested plant leaf samples through the instrument in a different random order on each of 5 different days. These determinations were made on the same digested solutions in order to eliminate variability in the weighing and digestion of the samples. The average relative standard deviation for the 39 samples was 0.66%. The relative standard deviation exceeded 1% for only 2 of the samples. Thus, the precision of the instrument is quite good.

Accuracy was determined by comparing the nitrogen found in the National Bureau of Standards reference material 1571 (orchard leaves) with the certified value and by comparing the nitrogen found with the instrument with that found by distillation and titration for ten samples of deciduous fruit tree leaves. The mean nitrogen concentration and standard deviation found for the Bureau of Standards sample was 2.72±0.02% (eleven determinations). The certified value of this sample is 2.76±0.05%. The results comparing instrumental with distillation-titration methods are tabulated in Table I. The determinations by the two methods were carried out on the same digested samples to eliminate variability in the weighing and digestion of the samples. There is no significant difference between the methods.

TABLE I
COMPARISON OF INSTRUMENT NITROGEN DETERMINATION WITH DISTILLATION-TITRATION FOR DIGESTED LEAF SAMPLES

| Sample | % N Instrumental | Distillation-Titration |
| --- | --- | --- |
| Apple | 2.21 | 2.24 |
| Pear | 2.27 | 2.26 |
| Peach | 2.55 | 2.55 |
| Almond | 1.62 | 1.62 |
| Mixed Species | 2.17 | 2.14 |
| Prune | 2.70 | 2.69 |
| Prune | 2.94 | 2.93 |
| Prune | 2.25 | 2.29 |
| Prune | 2.11 | 2.10 |
| Prune | 2.33 | 2.34 |
| Mean | 2.315 | 2.316 |
| Mean difference | 0.001 | |

Response to low concentrations of ammonium ion

The usefulness of the apparatus for determination of ammonium in water samples depends on its response to low concentration of ammonium. The lower limit of response is determined by the changes in electrical conductivity as ammonia dissolves in water. The conductivity is a function of the concentrations of ammonium, hydroxide and hydrogen ions. Additional of ammonia decreases hydrogen and increases ammonium and hydroxide ion concentrations. Hydrogen is much more mobile than ammonium ion so the change in conductivity with the initial addition of ammonia is very small. This can be shown by calculating the specific conductivity from the limiting ionic mobilities of the three ions and the ammonia-water equilibrium.

Figure 5:
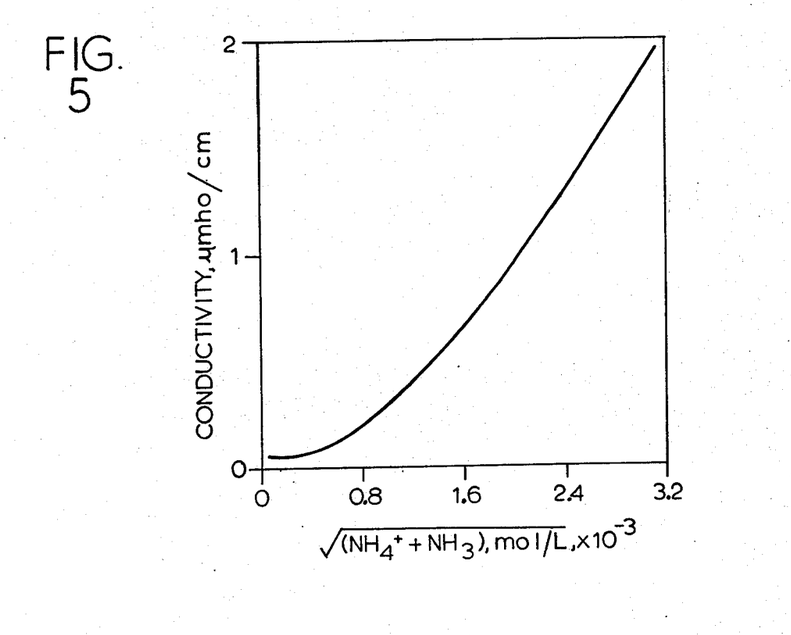
FIG. 5 is a graph showing calculated specific conductivity plotted against ammonia concentration.

FIG. 5 shows the calculated conductivity as a function of the square root of ammonia concentrations at 25°. The limiting ionic mobilities used were: H$^+$, 350; OH$^-$, 198; and NH$_4^+$, 73.4. The dissociation constant for ammonium hydroxide was taken as $1.77 \times 10^{-5}$. The figure shows the lag in response with the initial addition of ammonia. Calibration curves obtained with dilute ammonium standards were consistent with the calculated response. When the sample, reagent and water pumping rates were 4.98, 1.17, and 0.96 ml/min the useful lower limit was about $10^{-5}$ M NH$_4^+$ in the sample. This is adequate for most routine water analysis.

EXAMPLE 2

Detection of total dissolved carbon dioxide

Conversion of the apparatus to determine total dissolved carbon dioxide may be accomplished by switching the reagent line from sodium hydroxide to an appropriate acid, to suppress other volatiles and enhance the volatility of carbon dioxide. Perchloric acid was used in this study. Sulfuric acid works equally well. Suitability for dissolved carbon dioxide determinations was tested by comparing results for six drain water and well water samples with carbonate plus bicarbonate concentrations determined by titration. Concentrations of carbonate and bicarbonate were computed from total dissolved carbon dioxide determined by the instrument, the dissociation constants of carbonic acid and the pH of the water samples. Standards were prepared from sodium bicarbonate. The results are tabulated in Table II. The agreement between the methods is adequate for routine water analysis.

TABLE II
COMPARISON OF INSTRUMENTAL DETERMINATION OF CARBONATE PLUS BICARBONATE WITH RESULTS FROM TITRATION
$CO_3^= + HCO_3^-$, meq/l

| Sample | Instrumental | Titration |
|---|---|---|
| Drain water 1 | 6.69 | 6.8 |
| 2 | 5.65 | 5.4 |
| 3 | 4.56 | 4.8 |
| 4 | 6.35 | 6.1 |
| Well water 1 | 7.50 | 7.2 |
| 2 | 7.91 | 7.6 |
| Mean | 6.44 | 6.32 |
| Mean difference | 0.12 | |

Volatile acids or bases that would diffuse through the silicone fibers will interfere with carbon dioxide or ammonium determinations. Nitrate, chloride and sulfate salts produced no response when the instrument was set up for carbon dioxide determinations. Acetate, an ion that is uncommon in water samples, did produce a response and would interfere. Volatile amines are the most significant interferences in ammonium determinations. A test of interference from methylamine and dimethylamine showed a greater instrument response to these compounds than to ammonium solutions of the same concentration. In fact, the instrument can be used to detect these materials, when solutions of them are mixed with sodium hydroxide. Sample color and turbidity have no effect on performance of the instrument.

Maintenance of the apparatus

The instrument requires little maintenance beyond periodic replacement of the pump tubes. A hollow fiber unit has shown no signs of deterioration after twenty months of fairly constant experimental use. The electrical conductivity detection system requires much less electrical shielding than potentiometric devices. There is no detectable drift in the baseline after a five to ten minute warmup period. The maximum drift in response to standards observed was about one percent over a three-hour period. Segmenting the sample stream with air shortens the response time but the instrument can be operated without air injection if slightly longer sampling times are used. There is no need for debubbling the sample stream. The instrument is readily adapted to different concentration ranges by changing the sensitivity of the conductivity meter or by changing the size of the sample and reagent pump tubes.

Additional applications

Additional applications of the instrument are quite feasible. Adaptation to continuous sampling presents no problem. The instrument responds to atmospheric carbon dioxide when air is pumped in place of sample and reagent so it may have use in gas analysis. It may be possible to use it for nitrate determinations by passing the sample stream over a bed of Devarda alloy to convert nitrate to ammonia in a manner similar to that described by Mertens et al in 47 *Anal. Chem.*, 522–526 (1975).

EXAMPLE 3

Detection of sulfite ion

Figure 6:
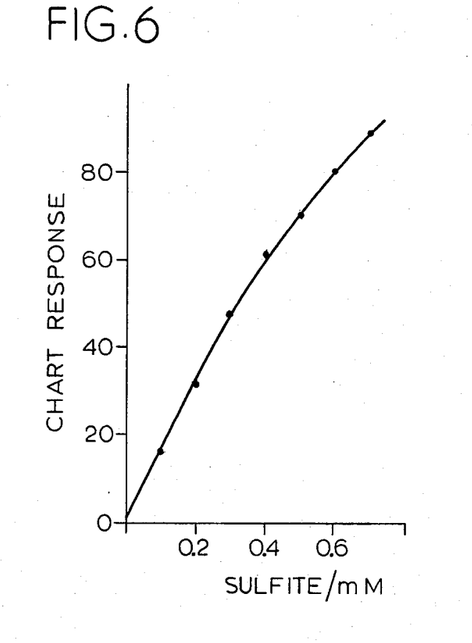
FIG. 6 is a graph with millimolar sulfite ion plotted against chart values obtained using a device embodying the present invention.

Solutions of sodium sulfite were pumped in 1:1 mixture with 2 N sulfuric acid. The response obtained is shown in the curve in FIG. 6. Note that the concentration range is submillimolar. The blank reading is very low, so that scale could be expanded to determine even lower concentrations. There appears to be no reason for the instrument not to respond to gaseous sulfur dioxide if gas containing sulfur dioxide were passed through the sample channel.

EXAMPLE 4

Detection of nitrite ion

Figure 7:
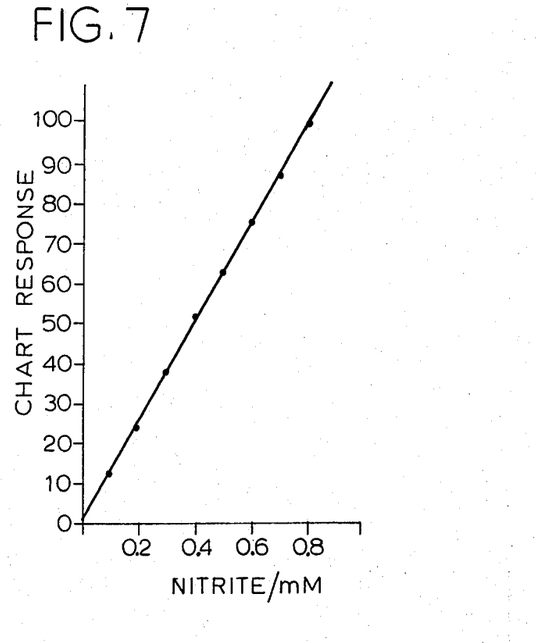
FIG. 7 is a graph obtained by the invention, with millimolar nitrite plotted against chart magnitudes.

Solutions of sodium nitrite were pumped through the instrument in 1:1 mixtures with 2 N sulfuric acid. The response obtained is shown in the curve in FIG. 7. As with sulfite, very good response was obtained with submillimolar concentrations and the blank is low; so even lower concentrations can be determined. These are at least two procedures for reducing nitrate to nitrite that can be incorporated into the instrument to allow its use for nitrate determination. Another possibility discussed earlier is the reduction of nitrate to ammonium with a column of Devarda alloy.

EXAMPLE 5

Detection of formic acid or formate salts

Figure 8:
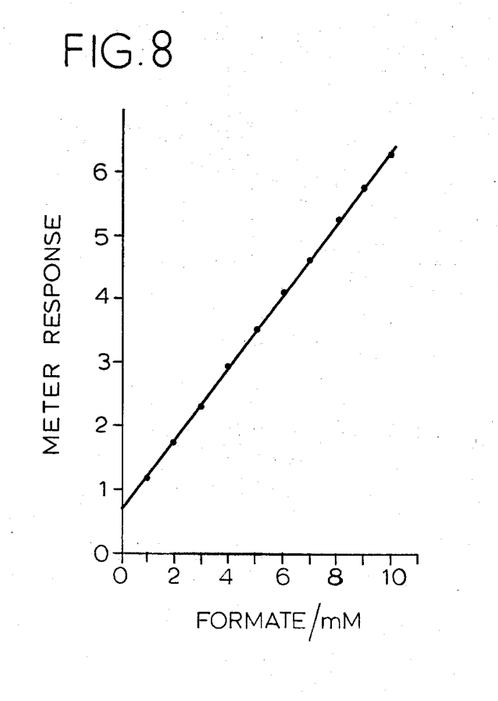
FIG. 8 is a graph obtained from the invention, with millimolar formate plotted against meter magnitudes.

Solutions of sodium formate were pumped through the instrument in 1:1 dilution with 2 N sulfuric acid. The response is shown in FIG. 8. The concentration range studied ranges from 0 to 10 millimolar. Thus, the sensitivity is not as great as with sulfite and nitrite. Nonetheless, this is a useful concentration range for many purposes.

EXAMPLE 6

Detection of acetic acid or acetate salts

Figure 9:
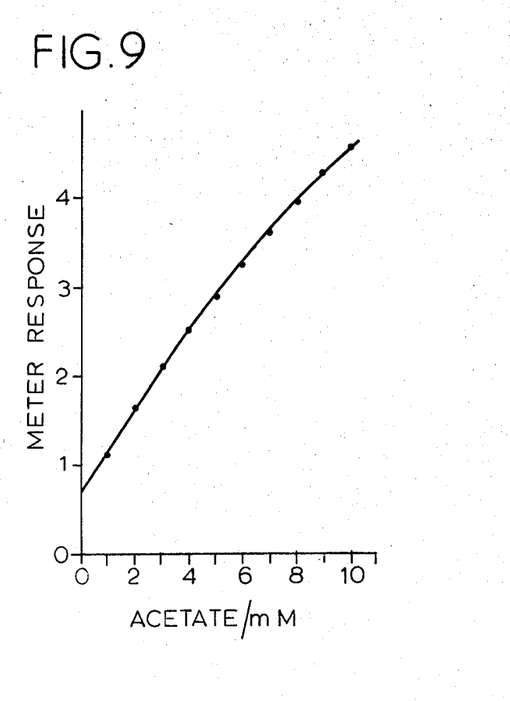
FIG. 9 is a graph obtained from the invention, with millimolar acetate plotted against meter response.

Sodium acetate was pumped through the instrument in 1:1 dilution with 2 N sulfuric acid. The response is shown in FIG. 9. The response is similar to that of formate (0 to 10 millimolar concentrations) and, again, this is a useful range for many purposes.

EXAMPLE 7

Detection of trichloroacetic acid or trichloroacetate salts

Figure 10:
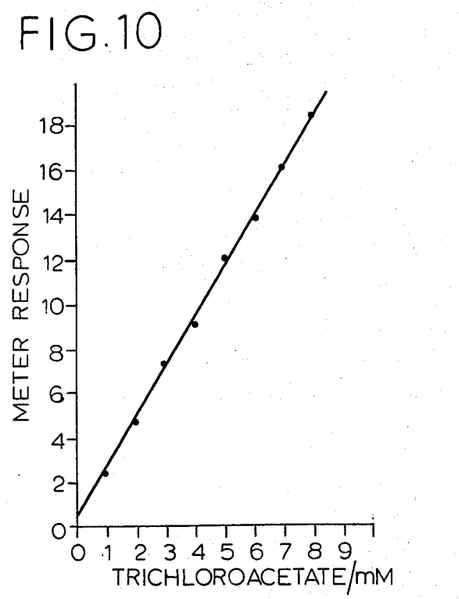
FIG. 10 is a graph obtained by using the invention, will millimolar trichloroacetate plotted against meter response.

Trichloroacetic acid was pumped through the instrument in 1:1 dilution with 2 N sulfuric acid. The response is shown in FIG. 10. The response to trichloroacetic acid was greater than the responses to formate or acetate, as judged by sample response relative to blank response.

The instrument appears to be useful also for other volatile electrolytes (other organic acids, etc.).

Figure 11:
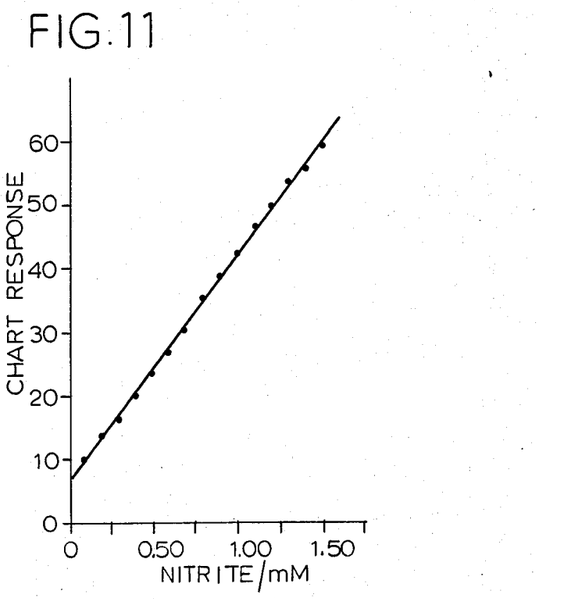
FIG. 11 is a graph made using a modified form of the invention with a silicone rubber membrane, with millimolar nitrite plotted against chart response.
Figure 13:
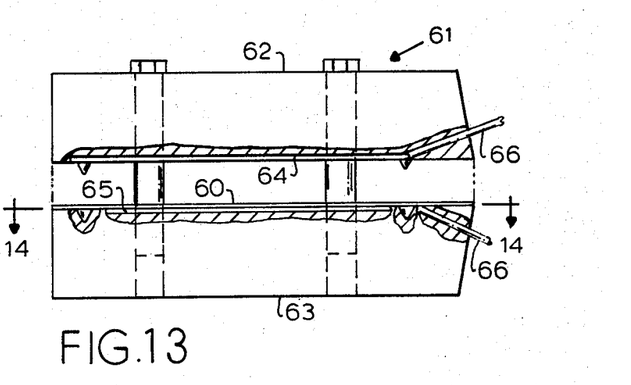
FIG. 13 is an exploded view of a transfer cell embodying a modified form of the invention.
Figure 14:
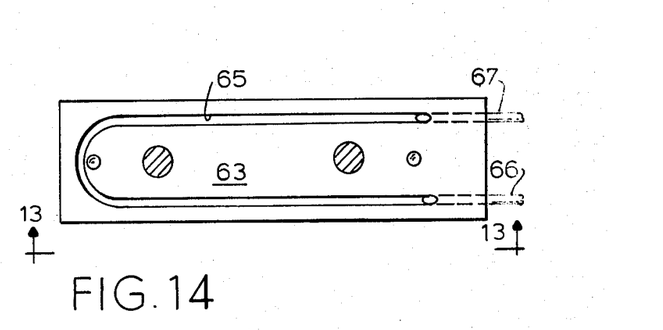
FIG. 14 is a view in section taken along the line 14—14 in FIG. 13.

While silicone rubber hollow fibers work very well, they are not essential. Preliminary work with a small dialysis cell containing a Teflon-impregnated fiberglass membrane to separate the sample and water streams indicates that a suitable gas diffusion unit may be built with them. For example, a silicone rubber membrane 60 (Gamma Enterprise's No. G157-B129-01) was mounted in a 6-inch dialyzer assembly 61, such as is available from Gamma Enterprises, Inc., Mt. Vernon, N.Y. (catalog numbers G177-B077 and G177-B008). The assembly is shown in FIGS. 13 and 14. There are two body members 62 and 63 providing two channels 64 and 65, each with an inlet 66 and an outlet 67. The solution goes through one channel 64 and the water through the other channel 65 and on to the conductivity cell. Sodium nitrite was pumped in 1:1 dilution with 2 N sulfuric acid. The test results with sodium nitrite are shown in FIG. 11. Note that the concentration range is higher than that used for nitrite with the hollow fibers. The blank is also higher; so it would be difficult to use this arrangement for very low concentrations.

Figure 12:
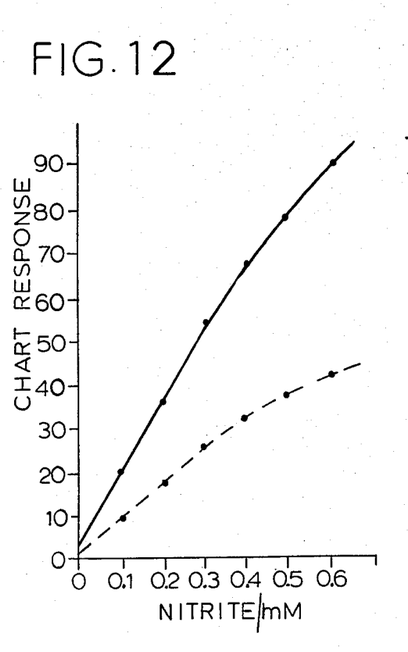
FIG. 12 shows similar graphs made with two modified forms of this invention employing two different types of membrane of polytetrafluoroethylene.

Still other membranes may be used, such as silicone sheet or film membranes in a dialysis cell, or other hydrophobic, gas-permeable materials. It is possible to use a porous hydrophobic material such as Teflon filter discs or sheets with small pore size to separate the sample stream from the water stream. This, in effect, creates an air gap between the streams, through which the volatile component can diffuse and thus be transferred from the sample stream to the solvent (collector) stream. For example, fluoropore is a filter membrane made from polytetrafluoroethylene (PTFE) bonded to a polyethylene net (Millipore Corp., Bedford, Mass.). The pores in this membrane are very small and the PTFE is hydrophobic; solution will not pass through it unless the pressure differential is very large. However, gases can readily diffuse through the pores and thus, be transferred from the sample stream to the water stream. The response to nitrite (same test as for silicone rubber) with the fluoropore membrane mounted in the dialysis cellis shown in solid lines in FIG. 12.

The same experiment was run with Mitex, a filter membrane fabricated by fusing together a mat of Teflon microfibers, a product of the Millipore Corp. Like fluoropore, it is hydrophobic, but gases can diffuse through the fibers. The response to nitrite with the Mitex membrane mounted on the dialysis cell is shown in a broken line in FIG. 12.

Manual operation

The device may be operated manually by presenting the sample to the sample tube in the pump 22 manually. Automatic samplers are very convenient, but are not essential. At the same time, the instrument is very well adapted to continuous monitoring rather than discrete sampling of a series of samples.

The readout response can be noted manually from a conductivity meter instead of using a strip chart recorder. This is not nearly as convenient but is possible. Alternatively, a data printer, or magnetic tape, or punched paper tape, may be used for data logging in place of a strip chart recorder. Components may be added to convert the output response to desired concentration units (e.g., microprocessors, minicomputers).

Miscellaneous comments

Air bubbles may be injected into the sample stream 10 to shorten the response time, but, as noted above, this is not crucial; the instrument works very well without injecting air. Some prior art requires injection of air and debubbling before the stream reaches the detector. If air is injected, it is not necessary to debubble the sample stream before it reaches the detector 18 with an instrument of this invention.

While the magnetic stirring-bar mixer 12 has been used and has been found very efficient, other mixers may also be used.

The instrument can easily be expanded for multichannel operation. For example, with an eight-channel pump, two hollow fiber units, two conductivity cells and meters, and two chart recorders, ammonium and dissolved carbon dioxide may be determined simultaneously on samples of water, waste water, etc.

The dimensions are not inflexible. A micro version that would consume very little sample is quite possible. Sample consumption is already quite small.

It may also (under special circumstances) be possible to inject the sample mixed with reagent into the channel surrounding the fibers rather than use continuous flow of sample and reagent. This would use very little sample.

The invention may employ a non-flowthrough conductivity detector system. Here the sample stream is separated by a permeable membrane from conductivity electrodes that are coated with a solvent. Response depends on the solvent equilibrating with the ammonia (carbon dioxide, etc.) in the sample stream.

Pulsed operation of the detector system may be useful for samples with very low concentrations of substance to be determined. Here, the solvent in the fibers is allowed to accumulate the substance to be determined and then pulsed through the flow-through conductivity cell to produce a greater response than would be the case in a continuously flowing system. This entails more complicated equipment and hence is more costly.

Pumping rates can all be easily and quickly varied to alter sensitivity, thus giving great flexibility to adapting to samples of widely different nature.

Chemical reactions can be incorporated into the sample plus reagent stream to convert substances that do not produce a response into substances that do produce a response. A reagent that enhances the measurement of the desired volatile material is also desirable. Preliminary work indicates that this should be feasible for nitrate. Inserting a small bed of Devarda alloy into the sample stream converts nitrate to ammonia, and this enables the instrument to be used for nitrate determination. There are probably other possibilities of this sort.

It may be possible to add reagents to the collector (solvent) stream that would react with substances passing through the membrane to enhance the response or to produce a response where one would not be obtained with a reaction in the collector stream.

I claim:

1. A method for determining the amount of volatile electrolyte present in an aqueous liquid sample, comprising:
    transferring volatile electrolyte from said sample into a second liquid of known electrical conductivity through a gas-permeable hydrophobic membrane that does not pass the aqueous liquid, during a predetermined time interval, and
    then determining the change in electrical conductivity in said second liquid resulting from such transfer.

2. The method of claim 1 wherein said transferring is done at substantially atmospheric pressure.

3. A method for determination of the amount of a particular type of volatile electrolyte present in an aqueous liquid sample comprising:
    adding to said sample a material that suppresses volatile electrolytes other than the type being tested for,
    transferring only unsuppressed volatile electrolyte from said sample into deionized degasified water at the same temperature during a predetermined time interval, and then determining
    then determining the conductivity of said water.

4. The method of claim 3 wherein said adding step comprises adding to said sample a material that both suppresses volatile electrolytes other than the type being tested for and enhances the volatility of the particular type of electrolyte being tested for.

5. A method for determination of the amount of a particular type of volatile electrolyte present in an aqueous liquid sample comprising:
  mixing said sample with a reagent that converts into non-volatile substances those volatile electrolytes which may be present in said sample that are of types different from said particular type,
  adjusting the resultant mixture to a predetermined temperature at which said particular electrolyte is suitably volatile,
  adjusting a predetermined amount of deionized, degasified water to said predetermined temperature,
  placing said sample and said deionized degasified water at said predetermined temperature in conjunction while separating them from each other by a liquid-impermeable, gas-permeable hydrophobic membrane,
  transferring said particular volatile electrolyte from said sample into said water through said membrane, and
  then afterwards determining the conductivity of said water.

6. The method of claim 5 including after the mixing step and before the adjusting steps, subjecting the sample to turbulent, not laminar, flow.

7. The method of claim 5 wherein said mixing step includes adding a reagent that enhances the volatility of the particular type of electrolyte being tested for.

8. A method for determination of the amount of a particular type of volatile electrolyte present in an aqueous liquid sample stream, comprising:
  mixing said sample stream at constant flow with a reagent at constant flow, said reagent being one that converts volatile electrolytes which may be present in said stream of types different from said particular type into non-volatile substances,
  adjusting the resultant sample stream to a predetermined temperature at which said particular electrolyte is suitably volatile,
  purifying a stream of deionized water to remove foreign substances and particulate matter therefrom,
  adjusting the purified stream of water to said predetermined temperature,
  degasifying said purified stream of water,
  passing said sample stream and said purified degasified water at said predetermined temperature along a path while separating them from each other by a liquid-impermeable, gas-permeable membrane,
  transferring volatile electrolyte from said sample stream into said water through said membrane, and
  then afterwards determining the conductivity of said water stream.

9. The method of claim 8 wherein said streams are subjected to turbulent, not laminar, flow during said adjusting, purifying, degassifying, and passing steps.

10. The method of claim 8 wherein said mixing step includes adding a reagent that enhances the volatility of the particular type of electrolyte being tested for.

11. Apparatus for determining the amount of a particular type of volatile electrolyte in an aqueous liquid sample, comprising:
  sample supply means for supplying an aqueous liquid sample,
  reagent supply means for supplying to said sample a reagent for suppressing other types of volatile electrolytes,
  mixing means connected to said supply means and in contact with said sample for mixing said sample with said reagent, prior to introduction of said sample to a permeation means,
  permeation means connected to said mixing means defining an isolated volume of substantial length divided into first and second plenum chambers by hydrophobic membrane means for preventing passage of aqueous liquid therethrough and for passing a gas therethrough,
  degassed water supply means connected to said permeation means,
  means for applying pure degassed water from said degassed water supply means to said first plenum chamber,
  means connected to said mixing means for applying said sample to said second plenum chamber, and
  a conductivity cell connected to said first plenum means and having electrical means for contact with said water for determining the electrical conductivity of the water after transfer of gas from said sample to said degassed water.

12. Apparatus for determining the amount of a particular type of volatile electrolyte in an aqueous liquid sample stream, comprising:
  permeation means defining an isolated path of substantial length and including hydrophobic liquid-impermeable, gas-permeable membrane means along the full length of said path dividing said path into first and second plenum chambers, said membrane preventing passage of liquid therethrough, while passing gas therethrough,
  feed means for feeding at least three liquids, namely water, a sample stream, and a reagent for changing other types of volatile electrolytes into non-volatile substances, to said permeation means,
  pumping means associated with said feed means for pumping said three liquids at a constant rate to said permeation means,
  mixing means, downstream of said means for pumping and connected thereto, for mixing said reagent with said sample stream in a constant proportion,
  purifying means, downstream of said means for pumping and connected thereto, for deionizing said water and removing particulate matter therefrom,
  heat-exchange means, downstream of said mixing means and said pumping means and connected thereto, for simultaneously bringing to the same predetermined temperature the purified water and the reagent-reacted water stream and maintaining said path at said predetermined temperature,
  degassing means associated with said heat-exchange means and in contact therewith for removing substantially all gas from said water stream,
  said pump means being upstream of and connected to said degassing means and said mixing means for passing said water stream into said first plenum chamber and said sample stream into the said second plenum chamber for flow along said path on opposite sides of said membrane means from each other, and
  an electrical conducting cell downstream of said permeation means and connected to said first plenum chamber for determining the electrical conductivity of the water stream after it leaves said path.

13. The apparatus of claim 12 wherein said sample stream and said water stream are conducted from step to step through tubing having a diameter such that turbulent flow is obtained rather than laminar flow.

14. The apparatus of claim 12 wherein said transfer means comprises a single tube and several strands of hollow silicone rubber fibers in said tube, said hollow fibers constituting said membrane means, the sample flowing in the tube around the fibers and the water flowing through the fibers.

15. Apparatus for determining the amount of a particular type of volatile electrolyte in an aqueous liquid sample, comprising:
- sample supplying means for supplying an aqueous liquid sample containing volatile electrolytes,
- reagent supplying means for separately supplying a reagent for changing other types of volatile electrolytes in said sample into non-volatile substances,
- mixing means connected to said sample supply means and to said reagent supply means, for mixing said sample and said reagent,
- degassed water supply means for supplying a predetermined amount of pure, degassed water,
- permeation means defining an isolated volume of substantial length, said volume being divided into first and second plenum chambers by hydrophobic membrane means for preventing passage of aqueous liquid therethrough while passing a gas therethrough,
- feeding means connecting said first plenum chamber to said degassed water supply means,
- feeding means connecting said second plenum chamber to said mixing means,
- conductivity cell means connected to said first plenum chamber and having electrical means in contact with said water after it flows through said first plenum chamber for determining the electrical conductivity of the water after transfer of gas from said sample to said water, and
- heat-exchange means in contact with said permeation means and said conductivity cell means for bringing both said sample and said degassed water to the same predetermined temperature and maintaining them at that temperature in said permeation means and in said conductivity cell means.

* * * * *